United States Patent [19]
Ward et al.

[11] Patent Number: 5,869,237
[45] Date of Patent: Feb. 9, 1999

[54] AMPLIFICATION KARYOTYPING

[75] Inventors: David C. Ward, Guilford, Conn.; Peter Lichter, Heidelberg, Germany

[73] Assignee: Yale University, New Haven, Conn.

[21] Appl. No.: 343,358

[22] Filed: Nov. 22, 1994

Related U.S. Application Data

[63] Continuation of Ser. No. 960,256, Oct. 13, 1992, abandoned, which is a continuation of Ser. No. 577,684, Sep. 4, 1990, abandoned, which is a continuation-in-part of Ser. No. 271,609, Nov. 15, 1988, abandoned.

[51] Int. Cl.$^6$ ............................. C12Q 1/68; C12P 19/34
[52] U.S. Cl. ................................. 435/6; 435/91.2
[58] Field of Search ................... 435/91.2, 6; 935/77, 935/78; 536/24.31, 24.33

[56] References Cited

PUBLICATIONS

Cotter, F.E. et al., "Rapid Isolation of Human Chromosome–Specific DNA Probes from a Somatic Cell Hybrid" *Genomics* 7:257–263 (1990).

Cremer, T. et al., "Detection of chromosome aberrations in the human interphase nucleus by visualization of specific target DNAs with radioactive and non–radioactive in situ hybridization techniques: diagnosis of trisomy 18 with probe L1.84" *Hum. Genet.* 74:346–352 (1986).

Cremer, T. et al., "Rapid Interphase and Metaphase Assessment of Specific Chromosomal Changes in Neuroectodermal Tumor Cells by in Situ Hybridization with Chemically Modified DNA Probes" *Exp. Cell Res.* 176:199–220 (1988).

Gray, J.W., et al., "Fluorescence Hybridization to Human Chromosome 21 Using Probes From a Charon 21A Library" Abstracts for the XII International Meeting of the Society for Analytical Cytology, Cambridge, England, 9–15 Aug. 1987, *Cytometry* Suppl.1:4, Abstract No. 19.

Landegent, J.E. et al., "Use of whole cosmid cloned genomic sequences for chromosomal localization by non–radioactive in situ hybridization" *Hum. Genet.* 77:366–370 (1987).

Ledbetter, S.A. et al., "PCR–Karyotype' of Human Chromosomes in Somatic Cell Hybrids" *Genomics* 8:614–622 (1990).

Ledbetter, S.A. et al., "Rapid Isolation of DNA Probes within Specific Chromosome Regions by Interspersed Repetitive Sequence Polymerase Chain Reaction" *Genomics* 6:475–481 (1990).

Lichter, P. et al., "Delineation of individual human chromosomes in metaphase and interphase cells by in situ suppression hybridization using recombinant DNA libraries" *Hum. Genet.* 80:224–234 (1988).

Litt, M. and R.L. White, "A highly polymorphic locus in human DNA revealed by cosmid–derived probes" *PNAS USA* 82:6206–6210 (1985).

Nelson, D.L. et al., "Alu polymerase chain reaction: A method for rapid isolation of human–specific sequences from complex DNA sources" *PNAS USA* 86:6686–6690 (1989).

Pinkel, D. et al., "Detection of structural chromosome abberations in metaphase spreads and interphase nuclei by in situ hybridization high complexity probes which stain entire human chromosomes" *Am. J. Hum. Genet.* 43 Suppl.3: A118, Abstract No. 0471 (1988).

Sealy, P.G. et al., "Removal of repeated sequences from hybridisation probes" *Nuc. Acids Res.* 13(6):1905–1922 (1985).

Soeiro, R. and J.E. Darnell, "Competition hybridization by 'pre–saturation' of HeLa cell DNA" *Chemical Abstracts* 71(25):195, Abstract No. 121640h (1969).

Soeiro, R. and J.E. Darnell, "Competition Hybridization by 'Pre–saturation' HeLa Cell DNA" *J. Mol. Biol.* 44:551–562 (1969).

*Primary Examiner*—George C. Elliott
*Assistant Examiner*—Thomas G. Larson
*Attorney, Agent, or Firm*—Elizabeth A. Hanley; Catherine J. Kara; Lahive & Cockfield, LLP

[57] ABSTRACT

A method is disclosed for determining the chromosomal identity of a sample of genomic DNA. The genomic DNA is amplified and labeled by polymerase chain reaction using primers substantially complementary to interspersed repetitive DNA sequences. The amplified and labeled genomic DNA fragments are then contacted with chromosomal DNA of known identity under conditions in which the chromosome-specific, but not the interspersed repetitive DNA sequences, of the amplified and labeled genomic DNA fragments are available for hybridization. Specific hybridization to chromosomal DNA of known identity determines the chromosomal identity of the sample of genomic DNA.

16 Claims, No Drawings

AMPLIFICATION KARYOTYPING

This application is a continuation of U.S. Ser. No. 07/960,256, filed on Oct. 13, 1992 (now abandoned), which is a continuation of U.S. Ser. No. 07/577,684, filed Sep. 4, 1990 (now abandoned), which is a continuation-in-part of U.S. Ser. No. 07/271,609, filed Nov. 15, 1988 (now abandoned).

GOVERNMENT SUPPORT

The work described herein was supported in part by the following grants from the National Institutes of Health: GM40633, GM40115 and GM41596.

BACKGROUND OF THE INVENTION

Human-rodent somatic cell hybrids are powerful reagents for human genome analysis. Gusella et al., *Proc. Natl. Acad. Sci. USA* 77: 2829–2833 (1980). Determination of the human DNA content of hybrids is typically done by conventional cytogenetic banding methods, isozyme analysis, or Southern blot analysis of a panel of DNA markers mapped to specific chromosomes. All of these methods are labor-intensive, and only a complete cytogenetic analysis assays for the presence or absence of whole chromosomes. However, the sensitivity of conventional cytogenetic methods is limited, and small pieces of human chromatin may go undetected or not be accurately identified as to chromosome of origin.

Recently, a method was described by Nelson et al. (*Proc. Natl. Acad. Sci. USA* 86: 6686–6690 (1989)) for specific amplification of human DNA in somatic cell hybrids using the polymerase chain reaction (PCR) and primers directed at the human-specific portion of Alu, a short interspersed repetitive element (SINE) present in approximately $10^6$ copies in mammalian genomes. Using a single Alu primer, amplification will occur whenever two Alu elements are less than 5 kilobases apart and lie in inverted orientation to each other. This strategy has been extended (Ledbetter et al., *Genomics* 6: 475–481 (1990)) to the second major class of interspersed repetitive sequence, the L1 element, a long interspersed repetitive sequence (LINE) present in $10^4$–$10^5$ copies per genome in mammals. Use of a primer directed at the human L1 sequence, L1Hs, produces fewer amplification products than with Alu, consistent with its lower abundance in the genome. Thus, human DNA amplification in inter-specific hybrid cells can be achieved by PCR using primers directed at human-specific sequences of different classes of interspersed repetitive sequences (IRS-PCR).

Ledbetter et al. (*Genomics* 6: 475–481 (1990)) also demonstrated the utility of PCR amplification from primers complementary to interspersed repeated sequences for analysis of the human component of a somatic cell hybrid. By running the amplification products on a gel, it was observed that a series of chromosome specific discrete bands were produced reproducibly. This is a simple and reproducible technique which does not require labeling of the PCR amplified product.

SUMMARY OF THE INVENTION

The subject invention relates to a method for identifying at least one chromosome or fragment thereof from a mammal. In the present method, the chromosome or fragment thereof is amplified and labeled, the amplification being accomplished by polymerase chain reaction, using primers which are substantially complementary to interspersed repeated DNA sequences in the genome of the mammal. The labeled amplified DNA is preannealed with competitor nucleic acid which contains sequences which are substantially complementary to the interspersed repeated DNA sequences, to suppress hybridization of the labeled amplified DNA to the interspersed repetitive sequences. That is, following preannealing, only non-repeated chromosome specific sequences are available for hybridization. The preannealed mixture is contacted with chromosome specific DNA from the mammal under conditions appropriate for intermolecular hybridization. Non-specifically bound nucleic acids are removed, and the specific hybridization of labeled amplified DNA to the chromosome specific DNA is detected.

In a preferred embodiment, the method is useful for the identification of at least one human chromosome or fragment thereof in a somatic cell hybrid. This method enables one to analyze the human component of a somatic cell hybrid which contains more than one human chromosome or fragment thereof. This was not possible using prior art amplification methods involving detection by electrophoretic display of the PCR reaction products because the pattern generated when more than one human component is present in a single somatic cell hybrid is too complex for analysis by electrophoretic display.

DETAILED DESCRIPTION OF THE INVENTION

The methods described herein are applicable to the identification of at least one mammalian chromosome or fragment thereof. Identification, as used herein, refers to the identification of a specific individual chromosome in the karyotype of the mammal which corresponds to the mammalian chromosome or fragment thereof. It is well known, for example, the nucleus of each human diploid cell contains 23 pairs of chromosomes. Using the methods described herein, one can identify an unknown chromosome as a member of a particular autosome pair (e.g., chromosome 1-22) or to the X or Y chromosomes. Similarly, a fragment of a chromosome can also be identified as being derived from a specific chromosome, provided that the fragment contains at least two interspersed repeated sequences which are close enough to each other to support amplification.

All mammalian chromosomes contain repeated sequences and unique sequences. The repeated sequences include both long and short interspersed repeat sequences. In humans, for example, the major family of short interspersed repeat sequences is denoted Alu repeat sequences. These repeats are found in apparently random locations throughout the human genome. It is estimated that the Alu repeats number approximately 900,000 in the haploid genome, giving an average distance between copies of approximately 4 kilobases.

The most common of the long interspersed repeat sequences in humans is the L1Hs element, also referred to as the KpnI sequence. It has been estimated that this sequence numbers approximately 10,000–100,000 copies in the human genome, either as complete or truncated versions of a 6.4 kilobase sequence.

In a preferred embodiment, the mammalian chromosome, or fragment thereof, to be identified is from a human. Initially, at least one chromosome, or fragment thereof, from a mammal is provided (e.g. in a buffered solution). The chromosome or fragment thereof can be essentially pure, or a component of a mixture of nucleic acids and other biomolecules. The chromosome or fragment thereof is then amplified as discussed below.

Primers can be designed which are substantially complementary to the interspersed repeat sequences contained within the mammalian chromosome or fragment thereof. As discussed above, in the human context this includes the Alu and L1HS interspersed repeat sequences. As used herein, substantially complementary primers do not necessarily share base for base complementarity to the interspersed repeat sequences. Rather, they are sufficiently complementary such that, under appropriate conditions, the primers anneal with the interspersed repeat sequences in a specific manner to form stable hybrids. Generally, such primers should be about 10 bases or more in length to form stable hybrids.

One skilled in the art will recognize that a mixture of primers which are complementary to distinct interspersed repeat sequences can also be used to practice this invention. For example, in humans, a mixture of primers which are complementary to the Alu and L1HS interspersed repeated sequences can be used to prime DNA amplification.

As described by Ledbetter et al. (*Genomics* 6: 475–481 (1990)), a nucleotide sequence for such primers has been identified for the amplification of human DNA. Furthermore, it has been shown that the human interspersed repeat primers referred to above are useful to prime the amplification of DNA sequences flanked by the interspersed repeat sequences using the well known polymerase chain reaction method. Mullis, U.S. Pat. No. 4,683,202. Each member of an interspersed repeat sequence pair must be close enough to the other to support amplification. Generally, this distance is about 5 kb or less. Given the teaching in the art, one skilled in the art could determine other appropriate sequences for the amplification of human DNA as well as appropriate sequences for the amplification of other mammalian DNAs using no more than routine experimentation.

Using appropriately designed primers, the mammalian chromosome or fragment thereof is amplified using conditions appropriate for the PCR amplification method. The amplified DNA is labeled with a reporter group to enable its detection in subsequent steps. Labeling can be accomplished in a number of ways, either during, or subsequent to, the amplification step. The reporter group can be any group which is specifically detectable including, for example, radioisotopes and non-isotopic reporter groups. Non-isotopic reporter groups include, for example, fluorochromes such as fluorescein, rhodamine, Texas red, Lucifer yellow, phycobiliproteins and cyanin dyes. Other non-isotopic reporter groups include specific binding pairs, such as biotin/avidin and haptene/antibody pairs. Methods for the attachment of such reporter groups to nucleic acid probes are well known to those skilled in the art, as are methods for their detection. See e.g. Lichter et al., *Nature* 345:93–95 (1990).

To label during the amplification step, deoxy-ribonucleic acid precursors are provided which carry a reporter group. During the amplification step, DNA polymerase incorporates labeled precursors into the amplification product, which can then be specifically detected in subsequent steps. To label subsequent to amplification, an enzyme (e.g., polynucleotide kinase) can be used to end label the amplification product with a detectable reporter group, as is well known in the art (see e.g. Maniatis et al., *Molecular Cloning, A Laboratory Manual*, Cold Spring Harbor (1982)).

Competitor nucleic acid is nucleic acid which contains regions which are complementary to the repeated sequences contained within the labeled amplified DNA. The competitor nucleic acid is preferably DNA. By annealing the competitor nucleic acid with the labeled amplified DNA, repeated sequences, which are present throughout the genome, form duplex regions which are unavailable for hybridization subsequently. Thus, hybridization to interspersed repetitive sequences which are present in all chromosomes of the mammal is suppressed. Only the chromosome-specific sequences are available for hybridization.

Competitor DNA is any DNA, all or a portion of which is complementary to repeated sequences in the genome of the mammal. Competitor DNA includes, for example, total genomic DNA, cloned repeated sequences, chemically synthesized repeated sequences, and Cot1 DNA.

Total genomic DNA can be isolated from any cell of the mammal. In the case of human chromosome analysis, total human genomic DNA is available from any cellular source. For example, placenta or white blood cells are particularly useful by virtue of their availability. This DNA can be prepared using known methods, such as those described by Davis et al. (*Basic Methods in Molecular Biology*, Elsevier, NY/Amsterdam (1986)). Preferably, it is digested using standard methods (e.g., DNAse treatment) to produce competitor fragments of about 500 base pairs or less. Further reduction to 200 bases or less may improve the specificity of the hybridization signal.

DNA sequences complementary to the repeated sequences of the mammal can be cloned into a DNA vector, propagated, and used as a supply of competitor DNA. Methods for isolating a sequence containing a repeat element and cloning the sequence into a DNA vector are well known to one of skill in the art. DNA sequences complementary to the repeated sequences can also be synthesized chemically. Several companies (e.g., Applied Biosystems) produce DNA synthesizers which are useful for this purpose.

Cot1 DNA is defined as that DNA fraction which, following denaturation, reassociates within one hour at a concentration of 10 $\mu$g/ml. Cot1 can be isolated by treating the mixture with nuclease S1 after a 1 hour reassociation period. Nuclease S1 specifically digests single stranded DNA. Alternatively, the reassociated DNA can be isolated by passing the mixture over a hydroxyapatite column which specifically binds double stranded DNA.

Labeled amplified DNA and competitor nucleic acid are combined in a buffered solution under conditions appropriate for preannealing. Preannealing, as used herein, refers to the formation of intermolecular hybrids between complementary regions of the labeled amplified DNA and the competitor nucleic acid. The concentration of the labeled amplified DNA is preferably in molar excess relative to target sequence in the chromosome-specific DNA to which specific hybridization is to be detected ultimately. The competitor concentration is adjusted such that theoretically the repeat sequences of the competitor are present in molar excess relative to the repeat sequences in the labeled amplified DNA.

Intermolecular hybridization refers to the formation of a duplex DNA molecule by the annealing of two complementary single stranded DNA molecules. The attractive force which drives hybrid formation is hydrogen bonding between complementary base pairs (adenine/thymine and guanine/cytosine). The thermal stability of intermolecular hybrids is affected, for example, by cation concentration and the presence of organic denaturants (e.g., formamide) in the buffered solution. One skilled in the art can select an appropriate buffered solution, containing a sufficient cation concentration and/or organic denaturant, to promote the formation of stable intermolecular hybrids between the labeled amplified DNA and the competitor nucleic acid within a predetermined temperature range. This solution, containing appropriate concentrations of labeled nucleic acid and competitor nucleic acid is heated to a temperature sufficient to denature duplex DNA (e.g., 100° for 3 minutes). The solution is then allowed to cool such that intermolecular hybrids are formed. It has been determined that a wide range of conditions and incubation times are appropriate for this preannealing step. For example; following denaturation, the preannealing solution can be maintained at a temperature of 37° for a period of approximately 1 hour.

The preannealed mixture is then contacted with chromosome specific DNA from the mammal under conditions appropriate for intermolecular hybridization. Chromosome specific DNA is DNA which will hybridize specifically with DNA from only one chromosome of the mammal under conditions in which hybridization to repeated sequences is suppressed. The chromosome specific DNA is segregated such that, for example, an observer is able to distinguish (e.g. visually or by instrumentation) between hybridization to chromosome 1 specific DNA and chromosome 2 specific DNA. This segregation can be accomplished in a variety of ways. For example, methods for treating cells such that chromosomes within the nucleus of the cells are fixed in situ on a support (e.g. a microscope slide) are well known in the art (see e.g., Cremer et al., *Hum. Genet.* 80:235–246 (1988)). Individual chromosome are resolveable and identifiable under an ordinary light microscope. For example, if labeled amplified DNA generated by amplification from a fragment of chromosome 1 is used to probe such a chromosome preparation under suppression conditions, specific hybridization to chromosome 1, but not to any other chromosome, is detected under a light microscope.

Many methods of fixation are known, or can be developed, by one of skill in the art. The cells can be at any stage of interphase or the mitotic or meiotic processes. In interphase cells, the genetic material is diffuse and threadlike, invisible with an ordinary light microscope. Dividing cells (i.e., those undergoing mitosis or meiosis) contain condensed chromosomes which are clearly visible and distinct when viewed with the aid of an ordinary light microscope. The specific detection of DNA complementary to a chromosome of interest is possible not only during cell division (mitosis and meiosis), but also during interphase.

In an alternative scheme, individual chromosome specific DNA libraries can be spotted onto a solid support as discrete chromosome specific dots, the position of each chromosome specific dot being preidentified. The construction of such libraries is well known in the art. Such libraries can be generated in an appropriate vector (e.g., bacteriophage). Individual chromosomes which are used to generate such libraries can be isolated by flow sorting or from somatic cell hybrids. Since DNA is negatively charged, a positively charged solid support (e.g. nitrocellulose paper or nylon membrane) is particularly useful. Following hybridization, an observer can detect specific hybridization to preidentified chromosome specific dots either visually, or using a device capable of detecting the signal generated by the particular reporter group employed.

The chromosome specific DNA need not be fixed in situ, so long as DNA corresponding to individual chromosomes is segragated. For example, the chromosome specific DNA libraries discussed above can be suspended in a hybridization buffer and placed in microcentrifuge tubes (each tube containing a chromosome specific DNA library). For example, in the case of human chromosome analysis, 24 individual sample tubes would be used corresponding to autosomes 1–22 and chromosomes X and Y. An aliquot of amplified labeled DNA can then be added to each tube under conditions appropriate for hybrid formation. In any tube which contains a chromosome specific sequence complementary to the labeled DNA, hybrid formation can be detected by analyzing the physical properties of molecules containing the reporter group.

For example, if each tube contains chromosome specific genomic clones in a bacteriophage lambda vector, hybridization of the amplified labeled DNA to the genomic clone can be detected by separating the hybridization products on a gel with appropriate control samples in adjacent lanes. In general, PCR amplified products primed from interspersed repeats are less than 5 kilobases in length. If this is run in a control lane in a gel, a series of discrete bands of less than 5 kilobases are detectable. If, on the other hand, the PCR product is complementary to, and formed a stable hybrid with genomic DNA cloned in lambda vector, the label is found in a much higher molecular weight range nearer the origin of the gel. The appearance of such a high molecular weight band containing the reporter group is indicative of the identity of the amplified chromosome or chromosomal fragment.

In a preferred embodiment, the preannealed mixture is contacted with the in situ preparation of a cell from the mammal. The preparation of such cells is described in Cremer et al. (*Hum. Genet.* 80:235–246 (1988)). The mixture is maintained at a temperature appropriate for intermolecular hybridization between complementary DNA sequences. Because the repeated sequences present in the amplified labeled DNA are unavailable for hybridization (due to the suppression step), the amplified labeled DNA forms intermolecular hybrids with the chromosome from the mammalian cell preparation which contains sequences complementary to the non-repeated sequences in the amplified labeled DNA.

After a sufficient incubation period, which can vary widely depending upon the particular conditions selected, non-specifically bound amplified labeled DNA is removed from the in situ cell preparation using any art-recognized method. Generally, the solution containing the amplified labeled DNA is removed from contact with the cell preparation and a wash solution is brought into contact with the cell preparation. The wash solution is incubated with the cell preparation under conditions that will not disrupt specifically bound amplified labeled DNA (e.g., DNA which is substantially complementary to the DNA to which it is bound), but which will disrupt non-specifically bound nucleic acid which is soluble in the wash solution. The wash solution is then removed from the cell preparation leaving, the specifically bound amplified labeled DNA.

The hybridization of amplified labeled DNA (i.e., specifically bound DNA) is then detected by appropriate methods. For example, in the preferred embodiment described above, if the labeled nucleic acid contains an isotopic reporter group, the in situ cell preparation is contacted with a photoreactive emulsion. Typically, this is accomplished by coating a microscope slide on which the in situ cell preparations are fixed, with a liquid photoreactive emulsion which is allowed to dry. Care is taken not to expose the emulsion to light. The slide is then stored in the dark for an appropriate exposure period. Radioactive decay during this exposure period results in a detectable chemical reaction in the emulsion which can be viewed under an ordinary light microscope. Fluorochrome labeled DNA can be detected, for example, by fluorescence microscopy and quantitated by photon counting devices. Methods for the detection of other non-isotopic reporter groups are well known in the art. See e.g. Lichter et al., *Nature* 345:93–95 (1990).

The methods described above are generally applicable to the identification of at least one mammalian chromosome or fragment thereof. A preferred embodiment enables the identification of at least one human chromosome or fragment thereof in a somatic cell hybrid. The construction and use of somatic cell hybrids is well known in the art. Gusella et al., *Proc. Natl. Acad. Sci. USA* 77: 2829–2833 (1980). Human somatic cell hybrids are propagatable cell lines which contain one or a few (generally less than 5) human chromosomes or fragments thereof. Typically, the cell is a murine cell.

By using the methods described above, characterization of the human component of these somatic cell hybrids is greatly simplified, as compared with classic cytogenetic methods. Total somatic cell hybrid DNA is isolated from the hybrid and amplified as described above. Probes specific for human interspersed repeats will not prime amplification of the hamster chromsomes. Following the steps described previously, this amplified DNA is contacted with chromosome specific human DNA, thereby facilitating the identification of the human component of the hybrid.

The identification of more than one mammalian chromosome or fragment thereof is carried out as described above. The detection of specific hybridization of amplified labeled DNA to chromosome-specific DNA corresponding to more than a single chromosome is diagnostic of the presence of more than one mammalian chromosome or fragment thereof.

The present invention is further illustrated by the following exemplification, which is not intended to be limiting in any way.

EXEMPLIFICATION

Human-rodent hybrid cell lines have been analyzed with regard to their human DNA content by using various DNA probe sets, derived from the hybrids, for in situ hybridization to normal human metaphase chromosome spreads. Total genomic hybrid DNA was compared with probe sets of hybrid DNA that were highly enriched in human sequences. The latter probes were obtained by amplification through the polymerase chain reaction (PCR) using oligonucleotide primers directed to human specific subsequences of the interspersed repetitive sequences (IRS) Alu and L1. Previously unidentified chromosomal material within hybrid lines was characterized with speed and precision. It is demonstrated that the complete human complement of hybrid lines can be rapidly assessed by comparing the data obtained with the Alu-PCR products with the results from the L1-PCR products or from the genomic hybrid DNA. This approach using IRS-PCR products is simple and fast and also provides an alternative way of generating complex DNA probe sets for the specific delineation of entire chromosomes or subchromosomal regions by in situ hybridization.

Materials and Methods

Cell Lines

Four human-hamster somatic cell hybrid lines containing a single intact human chromosome as shown by cytogenetic analysis were used in this study. Hybrid lines E1 and K1 were derived by 6-thioguanine selection of hybrids containing the human X chromosome plus other human chromosomes on a RJK88 Chinese hamster background. Analysis of 10 Giemsa banded and 20 G11 stained metaphase cells shows E1 to contain chromosome 7 and K1 to contain chromosome 22 as the only human chromosomes. Both hybrids have been submitted to the NICMS Human Genetic Mutant Cell Repository in Camden, NJ (E1=GM10790; K1=GM10888).

Hybrid TS-1 has been previously described (Nussbaum, R.L. et al., *Am. J. Hum. Genet.* 37:1192–1205 (1985)) and contains an intact human chromosome 18 and an unidentified metacentric marker chromosome of human origin in all cells examined. Hybrid EyeF3A6 (GM10027) has been previously described as containing chromosome 22 as its only intact human chromosome (Van Keuren, M.L. et al., *Cytogenet. Cell Genet.* 44:142–147 (1987)). Conventional cytogenetic analysis showed chromosome 22 in all cells, and one or two unidentified pieces of human chromosome material translocated to hamster chromosomes in each cell.

Chromosome Preparation

Metaphase chromosome spreads from stimulated human lymphocytes were prepared by standard techniques of colcemid treatment, hypotonic shock and methanol/acetic acid fixation as described (Cremer, T. et al., *Hum. Genet.* 80:235–246 (1988)). For in situ hybridization reactions, chromosomes were denatured in 70% formamide, 2×SSC for 2 min at 68° C., followed by incubation in 70%, 90% and 100% ice cold ethanol (3 min each) and air drying.

DNA Probes

Genomic DNA of the hybrid cell lines was isolated as described previously (Miller, S.A. et al., *Nucl. Acids Res.* 16:1215 (1988)). For PCR, 1 µg of hybrid DNA was used in 100 µl volume of 1 µM Alu primer 517 (Ledbetter, S.A. et al., *Genomics* 6:475–481 (1990)) or L1Hs primer (Nussbaum, R. L. et al., *Am. J. Hum. Genet.* 37:1192–1205 (1985)), 10 mM Tris-HCl, 50 mM KCl, 1.2 mM MgCl$_2$, 0.01% gelatin, 250 µM each of the four dNTPs and 2.5 units Thermus aquaticus polymerase (Perkin-Elmer/Cetus). After initial denaturation at 95° C. for 5 min, 30 cycles of PCR were carried out with denaturation at 94° C. for 1 min, annealing at 55° C. for 1 min and extension at 72° C. for 4 min (last extension 7 min). The products of each reaction were incubated with 1 unit of the large fragment of DNA polymerase 1 (Klenow fragment) at 37° C. for 20 min. After enzyme inactivation at 65° C. for 10 min, the DNA was ethanol precipitated. The pellet was resuspended in 60–70 µl of 10 mM Tris-HCl, 1 mM EDTA. PCR products were analyzed by agarose gel electrophoresis.

Previously mapped DNA clones were used in cohybridization experiments to confirm chromosome assignment: cosmid clone 519 (Watkins, P. C. et al., *Cytogenet. Cell Genet.* 40:773–774 (abstr.) (1985)) located on 21q (provided by P. Watkins); cosmid clone C31 (gift from I. Encio and S. Detera-Wadleigh) containing the human glucocorticoid receptor gene which is located on 5q (Wasmuth, J. J. et al., *Cytogenet. Cell Genet.* 51:137–148 (1989)); phage clone 7-1-558 containing sequences of the human immunoglobulin $V_H$ locus (Berman, J. E. et al., *EMBO J.* 7:727–738 (1988)) located on 14q (provided by F. W. Alt); phage clone FIX (gift from R. M. Kotin and M. Siniscalco) containing adeno-associated virus sequences which recognize specifically the cellular integration site on human 19q (Kotin, R. M. *Proc. Natl. Acad. Sci. USA* 87:2211–2215 (1990)).

All probe DNAs, genomic hybrid cell DNA, Alu-PCR or L1-PCR products and all but one previously mapped DNA probes, were labeled with biotin by nick translation (Langer, P. R. et al., *Proc. Natl. Acad. Sci. USA* 78:6633–6637 (1981)). Cosmid 519 was labeled with digoxigenin-11-dUTP (Boehringer Mannheim) by nick translation (Lichter, P. et al., *Science* 247:64–69 (1990)).

In Situ Hybridization and Probe Detection

Chromosomal in situ suppression (CISS) hybridization conditions were carried out as described elsewhere (Cremer, T. et al., *Hum. Genet.* 80:235–246 (1988)). Briefly, 2 μg of genomic hybrid DNA was combined with 2 μg total chinese hamster DNA, 2 μg total human DNA and 4 μg salmon sperm DNA, ethanol precipitated and resuspended in 10 μl of hybridization cocktail (50% formamide, 1×SSC, 10% dextran sulfate). Alternatively, when Alu-PCR or L1-PCR products were used as probe, 100 ng or 400 ng of probe, respectively, were combined with various combinations of competitor DNA: 2 μg human and 8 μg salmon sperm DNA, 10 μg human DNA, 10 μg human Cotl DNA (BRL/Life Technologies, Cat. No. 52795A) or 10 μg salmon sperm DNA. Probe denaturation, preannealing and hybridization was carried out as described (Cremer, T. et al., *Hum. Genet.* 80:235–246 (1988)). Following post hybridization washes and blocking with BSA, probes were detected via fluorescein isothiocyanate (FITC) conjugated to avidin. Probe 519 was detected by indirect immunofluorescence via Texas Red conjugated antibodies (Lichter, P. et al., *Science* 247:64–69 (1990)). No signal amplification procedure was applied. Chromosomes were counterstained with propidium iodide. Microscopic slides were evaluated by conventional epifluorescence microscopy. Digital images of specimens were generated as described (Lichter, P. et al., *Science* 247:64–69 (1990)).

Results

To compare the efficiency of total genomic DNA and IRS-PCR products for analyzing the human DNA complement of human-hamster hybrid cell lines, four independent hybrid lines were tested in a blind fashion. Probe sets were labeled with biotin and hybridized to normal human metaphase chromosomes followed by standard detection procedures using fluorescein labeled avidin. The IRS-PCR primers used in this study are expected to amplify DNA of different complexity. The Alu primer 517 was chosen because it usually results in a higher number of amplification products than other Alu primers. However, because of its location within the Alu repeat (Nelson, D. L. et al., *Proc. Natl. Acad. Sci. USA* 86:6686–6690 (1989)) this primer yields PCR products that contain high levels of Alu sequences. Therefore, Alu-PCR products were tested under CISS hybridization conditions using different competitor DNAs (0.2 mg/ml or 1 mg/ml total human DNA or 1 mg/ml human Cotl DNA). A specific signal could only be achieved using Cotl DNA as competitor whereas total human DNA was not sufficient to suppress the Alu sequences within this probe set. The location of the L1 primer at the 3' end of L1 repeats suggests that the L1-PCR products contain predominantly single copy sequences. However, CISS hybridization with and without human competitor DNA showed that there are repetitive sequences (most likely Alu sequences) amplified, and therefore human competitor DNA is required to achieve specific labeling.

The Alu-PCR products of two hybrid lines, designated GM10790 and GM10888, each labeled specifically only one chromosome, number 7 or 22, respectively. Chromosome assignment was achieved by DAPI banding for GM10790. In the case of GM10888, in addition to DAPI staining co-hybridization of the probe set with cosmid clone 519, previously mapped to chromosome 21, was carried out to distinguish between chromosomes 21 and 22. The target chromosomes are not evenly labeled but show an R-banding like pattern correlating with the occurence of Alu sequences along the chromosomes. The labeling of chromosome 7 in hybrid line GM10790 corresponds to the result seen with GM10790 genomic DNA. However, while the GM10888 genomic DNA probe revealed extensive labeling of chromosome 22, additional signals were observed in the centromeric region and on the short arms of the other D-and G-group chromosomes (chromosomes 13, 14, 15 and 21; compare cell line GM10027 below). Similar results were seen with the L1-PCR products. These additional signals are most likely due to known cross homologies of sequences in these chromosomal regions (e.g., Waye, J. S. and H. F. Willard, *Proc. Natl. Acad. Sci. USA* 86:6250–6254 (1989); Choo, K. H. et al., *Genomics* 5:332–344 (1989); Alexandrov, I. A. et al., *Chromosoma* 96:443–453 (1988); Jorgensen, A. L. et al., *Genomics* 3:100–109 (1988); Jorgensen, A. L. et al., *Proc. Natl. Acad. Sci. USA* 84:1075–1079 (1988); and Lo, Y. -M. D. et al., *Nucl. Acids. Res.* 16:8719 (1988)) and, therefore, do not reflect parts of the genome present in the hybrid line. The Alu-PCR products of line GM10888 did not label the centromeric region or the short arm of chromosome 22, most likely because of an underrepresentation of Alu sequences in this region (Moyzis, R. K. et al., *Genomics* 4:273–289 (1989)); hence, there is no cross hybridization to the other acrocentric chromosomes. The L1-PCR products of GM10888 label the entire chromosome 22, again generating a banding pattern, including the short arm of 22.

The analyses of hybrid cell lines TS-1 and GM10027 showed a more complex pattern with regard to the human DNA content. With total genomic DNA of hybrid line TS-1 strong fluorescent hybridization signals were observed labeling human chromosome 18 and the short arm of chromosome 5. To confirm the chromosome assignment for the second signal on the short arm of chromosome 5, cohybridization was carried out with DNA clone C31, previously mapped to the long arm of chromosome 5. A retrospective analysis of Giemsa-banded hybrid cells indicated that the previously unidentified marker chromosome of TS-1 is an iso(5p) chromosome. Additional hybridization signals, again most likely due to cross homology, were seen at the centromeres of several other chromosomes as well.

Both the Alu-PCR or L1-PCR products of TS-1 resulted in a highly specific delineation of chromosome 18 and 5p. The Alu-PCR products did not stain the centromeres of chromosomes 5,18 or any other chromosome, whereas the L1-PCR products stained the centromeric regions of chromosomes 5 and 18 but no additional centromere labeling was found. Thus, the IRS-PCR products resulted in highly specific hybridization signals without any significant cross hybridization.

When using genomic DNA of hybrid cell line GM10027 as a probe, a complete labeling of chromosome 22 and substantial labeling of chromosomes 19 (which is more strongly labeled on the short arm than on the long arm), 15 (short arm and proximal third of the long arm) and 14 (short arm) was observed. In addition to the predominantly labeled centromeres of these four chromosomes, there were again several other centromeres labeled. Cohybridization experiments with probes previously mapped to 14q and 19q, respectively (see Materials and Methods), were used to confirm the identity of chromosomes exhibiting hybridization signals. When the Alu-PCR product of GM10027 was used as probe, the results were the labeling of the long arm of chromosome 22, the short arm of 19 and the proximal third of the long arm of 15. Thus, not only the centromeres but also the regions of 22p, 15p and 14p are spared from decoration with the Alu-PCR probe. The staining of the short arm of chromosomes 14 and 15 with the genomic DNA probe can be interpreted as cross homologies of sequences on 22-. These data demonstrate that the previously unidentified translocated chromosome pieces in GM10027 can be attributed to the proximal part of 15q and to 19p. It should be noted that the Alu-PCR products from both cell lines containing chromosome 22 do not hybridize to 22p.

In conclusion, to obtain comprehensive data with regard to the human DNA content in human-rodent hybrid cell lines, comparison of the in situ hybridization results obtained with two probe sets, Alu-PCR products and genomic hybrid DNA or Alu-PCR and L1-PCR products, respectively, should prove to be a very powerful method for such karyotyping analysis.

Equivalents

Those skilled in the art will recognize or be able to ascertain, using no more than routine experimentation, many equivalents of the specific embodiments of the invention described herein. Such equivalents are intended to be encompassed by the following claims.

We claim:

1. A method for determining the chromosomal identity of mammalian-specific genomic DNA containing interspersed repetitive DNA sequences present in a nucleic acid sample, comprising the steps of:
   a) subjecting a nucleic acid sample containing mammalian-specific genomic DNA containing interspersed repetitive DNA sequences to polymerase chain reaction conditions using primers which are substantially complementary to at least one of the interspersed repetitive DNA sequences present in the mammalian-specified genomic DNA, to produce labeled amplified mammalian-specified genomic DNA fragments containing interspersed repetitive DNA sequences;
   b) combining
      i) a sample of the labeled amplified mammalian-specific genomic DNA fragments of step a);
      ii) chromosomal DNA of known identity; and
      iii) competitor DNA containing DNA sequences which are substantially complementary to at least one interspersed repetitive DNA sequence present in the mammalian-specific genomic DNA.
   under conditions appropriate for intermolecular hybridization, wherein hybridization between repetitive sequences in the labeled amplified mammalian-specific genomic DNA fragments and the chromosomal DNA of known identity is suppressed, thereby allowing hybridization between chromosome-specific sequences in the labeled amplified genomic mammalian-specific DNA fragments and the chromosomal DNA of know identity to occur; and
   c) detecting specific hybridization signals of labeled mammalian-specific genomic DNA fragments of the chromosomal DNA of known identity, wherein each detected signal is distinguishable and identified a specific chromosomal sequence present in the mammalian-specific genomic DNA containing interspersed repetitive DNA sequences, such that the chromosomal identity of the mammalian-specific genomic DNA containing interspersed repetitive DNA sequences present in the nucleic acid sample is determined.

2. A method of claim 1, wherein the labeled amplified mammalian-specific genomic DNA fragments and the competitor DNA are combined in step b), before the combination with the chromosomal DNA of known identity, under conditions which allow the repetitive DNA sequences in the labeled amplified mammalian-specific genomic DNA fragments and in the competitor DNA to preanneal.

3. A method of claim 1, wherein the interspersed repetitive DNA sequences comprise short interspersed repetitive DNA sequences.

4. A method of claim 3, wherein the short interspersed repetitive DNA sequences are Alu sequences.

5. A method of claim 1, wherein the interspersed repetitive DNA sequences comprise long interspersed repetitive DNA sequences.

6. A method of claim 5, wherein the long interspersed repetitive DNA sequences are human L1 elements.

7. A method of claim 1, wherein the chromosomal DNA of known identity comprises chromosomes fixed in situ.

8. A method of claim 1, wherein the chromosomal DNA of known identity comprises chromosomal libraries.

9. A method of claim 1, wherein the chromosomal DNA of known identity comprises segregated chromosomal DNA or fragments thereof.

10. A method of claim 1, wherein the chromosomal DNA of known identity comprises chromosomal DNA or fragments thereof are immobilized on a solid support.

11. A method of claim 1, wherein said nucleic acid sample is obtained from a hybird cell containing DNA from at least two different species of mammals and the chromosomal DNA of known identity comprises chromosomes or fragments thereof from one of said mammalian species.

12. A method of claim 1, wherein the competitor DNA is present at a concentration such that the repetitive sequences of the competitor DNA are present in molar excess relative to the repetitive sequences in the labeled mammalian-specific genomic DNA fragments.

13. A method of claim 1, wherein said mammalian-specific genomic DNA containing interspersed repetitive DNA sequences is human genomic DNA.

14. A method of claim 1, wherein said nucleic acid sample comprises total genomic DNA.

15. A method of claim 1, wherein said polymerase chain reaction conditions comprise a detectable reporter group.

16. A method for determining the chromosomal identity of human genomic DNA containing interspersed repetitive DNA sequences present in a somatic cell hybird, comprising the steps of:
   a) subjecting a human genomic DNA sample containing human genomic DNA containing interspersed repetitive DNA present in a somatic cell hybird to polymerase chain reaction conditions using primers which are substantially complementary to at least one of the interspersed repetitive DNA sequences in the human genomic DNA, to produce labeled amplified human genomic DNA fragments containing interspersed repetitive DNA sequences;
   b) combining a sample of the labeled amplified genomic DNA fragments of step a) with competitor DNA containing sequences which are substantially complementary to at least one interspersed repetitive DNA sequence present in the human genomic DNA, thereby rendering the chromosome-specific sequences but not the interspersed repetitive DNA sequences of the labeled amplified genomic DNA fragments available for further hybridization;
   c) combining the product of step b) with human chromosomal DNA of known identity, under conditions appropriate for intermolecular hybridization, wherein hybridization between repetitive sequences in the labeled amplified human genomic DNA fragments and the human chromosomal DNA of known identity is suppressed, thereby allowing hybridization between chromosome-specific sequences in the labeled amplified human genomic DNA fragments and the human chromosomal DNA of known identity to occur; and d) detecting specific hybridization signals of labeled amplified human genomic DNA fragments to the chromosomal DNA of known identity, wherein each detected signal is distinguishable and identifies a specific chromosomal sequences present in the human genomic DNA containing interspersed repetitive DNA sequences in a somatic cell hybird, such that the chromosomal identity of the human genomic DNA containing interspersed repetitive DNA sequences present in a somatic cell hybird is determined.

* * * * *

UNITED STATES PATENT AND TRADEMARK OFFICE
CERTIFICATE OF CORRECTION

PATENT NO. : 5,869,237
DATED : February 9, 1999
INVENTOR(S) : David C. Ward, et al.

It is certified that error appears in the above-identified patent and that said Letters Patent is hereby corrected as shown below:

On the title page,

In the "Inventors"

section (75) replace "Guilford" with --Madison--.

In the Claims:

Column 11, claim 1, line 42, change "." to --,--.

Signed and Sealed this

Fifth Day of September, 2000

Attest:

Q. TODD DICKINSON

Attesting Officer

Director of Patents and Trademarks